(12) United States Patent
Tsai

(10) Patent No.: US 10,413,271 B2
(45) Date of Patent: Sep. 17, 2019

(54) METHOD, SYSTEM AND DEVICE FOR AUSCULTATION

(71) Applicant: iMEDI PLUS Inc., Hsinchu (TW)

(72) Inventor: Kun-Hsi Tsai, Hsinchu County (TW)

(73) Assignee: iMEDI PLUS Inc., Hsinchu (TW)

( * ) Notice: Subject to any disclaimer, the term of this patent is extended or adjusted under 35 U.S.C. 154(b) by 974 days.

(21) Appl. No.: 14/943,037

(22) Filed: Nov. 17, 2015

(65) Prior Publication Data
US 2016/0143612 A1    May 26, 2016

Related U.S. Application Data

(60) Provisional application No. 62/082,563, filed on Nov. 20, 2014, provisional application No. 62/082,559, filed on Nov. 20, 2014.

(51) Int. Cl.
*A61B 7/04* (2006.01)

(52) U.S. Cl.
CPC ..................... *A61B 7/04* (2013.01)

(58) Field of Classification Search
CPC ..................................... A61B 7/04
See application file for complete search history.

(56) References Cited

U.S. PATENT DOCUMENTS

| | | | |
|---|---|---|---|
| 5,213,108 A | 5/1993 | Bredesen et al. | |
| 2002/0180716 A1* | 12/2002 | Kim | G11B 20/10 345/204 |
| 2002/0194029 A1* | 12/2002 | Guan | G06Q 10/10 705/3 |
| 2004/0076303 A1* | 4/2004 | Vyshedskly | A61B 5/0002 381/67 |
| 2004/0092846 A1* | 5/2004 | Watrous | A61B 7/04 600/586 |
| 2005/0157887 A1* | 7/2005 | Kim | A61B 7/04 381/67 |
| 2006/0169529 A1* | 8/2006 | Tamakoshi | A61B 7/04 181/131 |

(Continued)

FOREIGN PATENT DOCUMENTS

| CN | 101507613 | 8/2009 |
|---|---|---|
| CN | 101641050 A | 2/2010 |

(Continued)

*Primary Examiner* — Olisa Anwah
(74) *Attorney, Agent, or Firm* — Chieh-Mei Wang

(57) ABSTRACT

The present disclosure provides a medical/healthcare system which comprises an electronic stethoscope and a medical host under a medical/healthcare environment. The electronic stethoscope comprises an auscultation module for recording a sound from internal body of a patient to form an auscultation data, a reader for obtaining a patient information from the patient, a processor module to receive and associate the patient information to the auscultation data to form an auscultation file, a storage for storing the auscultation file, a display module to display the auscultation file for selection, a control input interface for selecting the auscultation file for playback, an output module for playing the auscultation file by outputting the sound corresponding to the auscultation file when selected, and a power module to provide electricity to all the others.

42 Claims, 13 Drawing Sheets

(56) References Cited

U.S. PATENT DOCUMENTS

| | | | |
|---|---|---|---|
| 2008/0221930 A1* | 9/2008 | Wekell | A61B 5/02055 |
| | | | 705/3 |
| 2009/0063737 A1* | 3/2009 | Ocasio | A61B 7/04 |
| | | | 710/104 |
| 2011/0087135 A1* | 4/2011 | Ferzli | A61B 7/04 |
| | | | 600/586 |
| 2011/0282168 A1* | 11/2011 | Weiss | A61B 5/742 |
| | | | 600/323 |
| 2012/0059669 A1* | 3/2012 | Whittenburg | G06Q 50/22 |
| | | | 705/3 |
| 2012/0310115 A1* | 12/2012 | Bedingham | A61B 7/04 |
| | | | 600/586 |
| 2013/0116513 A1 | 5/2013 | Smith | |
| 2013/0116584 A1* | 5/2013 | Kapoor | A61B 5/02 |
| | | | 600/513 |
| 2014/0107515 A1* | 4/2014 | Lee | A61B 7/026 |
| | | | 600/528 |
| 2015/0104027 A1* | 4/2015 | Mulumudi | H04R 1/46 |
| | | | 381/67 |
| 2015/0190110 A1* | 7/2015 | Chong | H04R 1/46 |
| | | | 600/528 |
| 2015/0201272 A1* | 7/2015 | Wong | H04R 1/46 |
| | | | 381/67 |
| 2016/0128646 A1* | 5/2016 | King | A61B 5/7475 |
| | | | 715/771 |

FOREIGN PATENT DOCUMENTS

| | | |
|---|---|---|
| CN | 202198586 | 4/2012 |
| CN | 102697520 A | 10/2012 |
| TW | 200724104 A | 7/2007 |
| TW | M462587 | 10/2013 |

* cited by examiner

METHOD, SYSTEM AND DEVICE FOR AUSCULTATION

FIELD OF THE DISCLOSURE

The present disclosure relates generally to a method, system and device for auscultation, more specifically an electronic stethoscope not only records a sound from a patient but also obtains a patient information from the patient and/or an auscultation position 400 selected by a medical/healthcare provider.

BACKGROUND OF THE DISCLOSURE

Auscultation is a very common technique for diagnosis purpose around medical/healthcare environment. Traditionally, a medical/healthcare provider may use a stethoscope to listen to sound from internal body of a patient and manually keep a record of related information such as a patient information, diagnosis and/or description of the auscultation. The problem with keeping record manually is the possibilities of making mistake while doing so, especially wrongly recording the patient information, diagnosis and/or description of the auscultation.

Furthermore, traditional auscultation done by the medical/healthcare provider does not leave record of the sound from the internal body of the patient for later use. This brings inconvenience for the medical/healthcare provider to verify the result of auscultation such as diagnosis and/or description of the auscultation.

Last but not least, patient safety is not ensured under traditional auscultation when a patient's auscultation diagnosis and/or description is mismatched to another patient's ID.

According to the above, a method, system and device for auscultation which can record the sound from the internal body, patient information, diagnosis and/or description of the patient is needed to improve medical/healthcare service and reduce the time and possibilities of making mistakes from manually recording the above.

BRIEF DESCRIPTION OF THE DRAWINGS

The accompanying drawings illustrate one or more embodiments of the disclosure and together with the written description, serve to explain the principles of the disclosure. Wherever possible, the same reference numbers are used throughout the drawings to refer to the same or like elements of an embodiment, and wherein.

In accordance with common practice, the various described features are not drawn to scale and are drawn to emphasize features relevant to the present disclosure. Like reference characters denote like elements throughout the figures and text.

DETAILED DESCRIPTION OF THE DISCLOSURE

Figure 1:
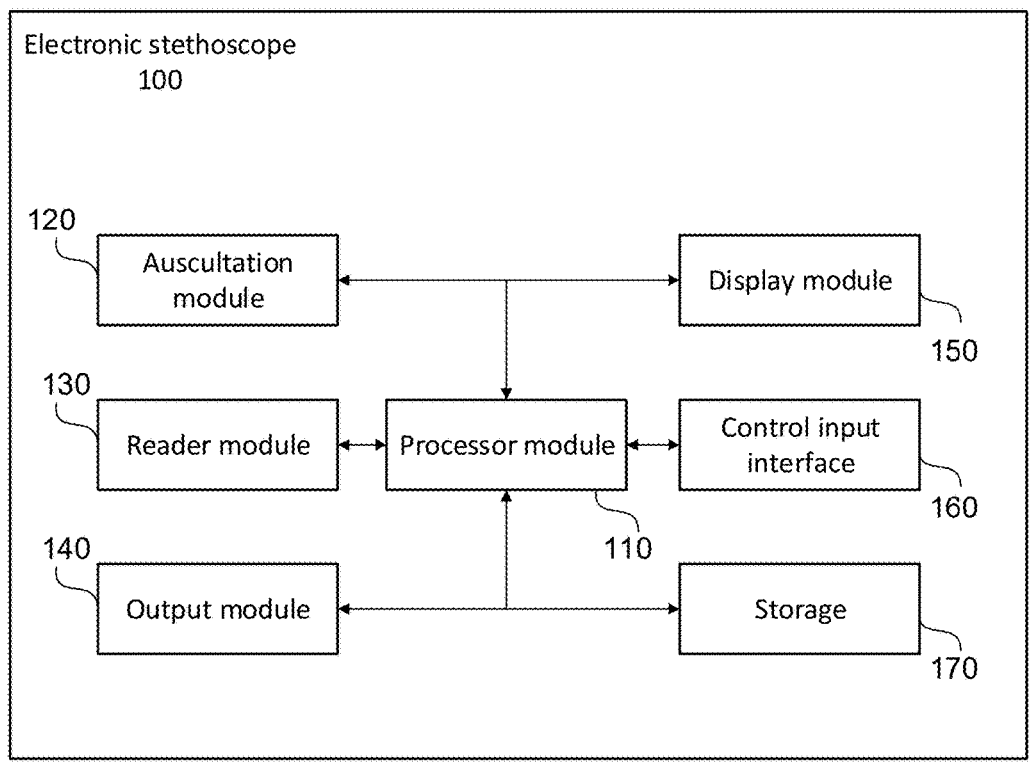
FIG. 1 is a schematic illustration of an example set of basic components of an electronic stethoscope according to one embodiment of the present disclosure.

The present disclosure will now be described more fully hereinafter with reference to the accompanying drawings, in which exemplary embodiments of the disclosure are shown. This disclosure may, however, be embodied in many different forms and should not be construed as limited to the embodiments set forth herein. Rather, these embodiments are provided so that this disclosure will be thorough and complete, and will fully convey the scope of the disclosure to those skilled in the art. Like reference numerals refer to like elements throughout.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," or "includes" and/or "including" or "has" and/or "having" when used herein, specify the presence of stated features, regions, integers, steps, operations, elements, and/or components, but do not preclude the presence or addition of one or more other features, regions, integers, steps, operations, elements, components, and/or groups thereof.

It will be understood that the term "and/or" includes any and all combinations of one or more of the associated listed items. It will also be understood that, although the terms first, second, third etc. may be used herein to describe various elements, components, regions, parts and/or sections, these elements, components, regions, parts and/or sections should not be limited by these terms. These terms are only used to distinguish one element, component, region, part or section from another element, component, region, layer or section. Thus, a first element, component, region, part or section discussed below could be termed a second element, component, region, layer or section without departing from the teachings of the present disclosure.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

The description will be made as to the embodiments of the present disclosure in conjunction with the accompanying drawings in FIGS. 1 to 8. Reference will be made to the drawing figures to describe the present disclosure in detail, wherein depicted elements are not necessarily shown to scale and wherein like or similar elements are designated by same or similar reference numeral through the several views and same or similar terminology.

Methods, systems and device for auscultation in accordance with various embodiments of the present disclosure provides auscultation in medical/healthcare environment, such as hospital, healthcare center, etc. In particular, various embodiments involve auscultating a patient, such as a healthy/sick person, livestock, pets, or other types of living beings. Although examples described herein relate to auscultation of a person's body area, for example a chest area, precordia area, abdomen area, extremity area, head area, neck area, or constituent thereof (e.g. lung, gastrointestinal system, aorta, tricuspid, brachial artery, femoral artery, trachea, jugular vein, temporal region, mastoid region, etc.). It is therefore appreciated that the disclosed technology is configured to auscultate other aforementioned forms of patient corresponding to one or more different portion of body area of the patient. Further, the present disclosure is configured to obtain a patient information and associate the patient information to the aforementioned auscultation done by a medical/healthcare provider.

An example set of basic components of an electronic stethoscope 100 according to one embodiment of the present disclosure as shown in FIG. 1. The electronic stethoscope 100 comprises a chestpiece 120 for recording a sound from internal body of a patient to form an auscultation data, a reader module 130 for obtaining a patient information from the patient, a processor module 110 to receive and associate the patient information to the auscultation data to form an auscultation file, a storage 170 for storing the auscultation file, a display module 150 for displaying a playlist corresponding to the auscultation file that is selected by a medical/healthcare provider from the playlist, a control input interface 160 for sending a playback signal to the processor module 110, an output module 140 configured to play the auscultation file by outputting the sound corresponding to the auscultation file which is selected by the medical/healthcare provider from the playlist using the control input interface 160, and a power module (not shown) to provide electricity to all the others. The processor module 110 is electrically connected to the chestpiece 120, the reader module 130, the storage 170, the display module 150, the control input interface 160, the output module 140, and the power module.

Figure 2:
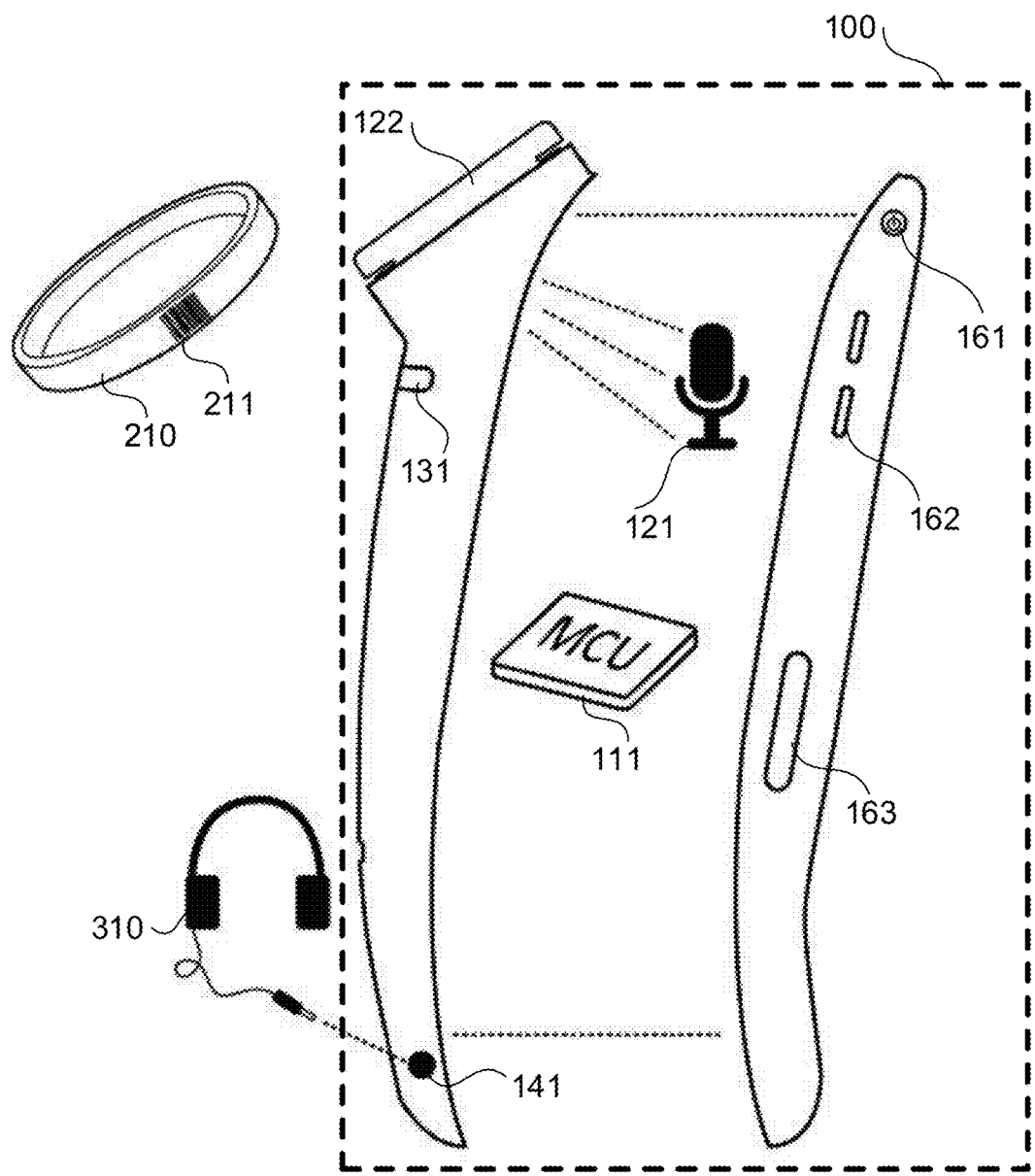
FIG. 2 is a schematic illustration of the electronic stethoscope according to one embodiment of the present disclosure.

FIG. 2 schematically illustrates an electronic stethoscope 100 which comprises various components shown in FIG. 1. In this embodiment of the present disclosure, the chestpiece 120 comprises a diaphragm 122 for resonating with the patient while the diaphragm 122 is in contact with the patient's body, and a microphone 121 for recording a sound from the patient's body to generate an auscultation data. It should be noted that the diaphragm 122 is configured to resonate with both high frequency and low frequency sound. The control input interface 160 comprises a recording button 161 which is configured to send a recording signal. As the recording signal is detected, the microphone 121 starts recording the sound from the patient's body to generate the auscultation data. The auscultation data is sent to the processor module 110 to be associated with a patient information, wherein the processor module 110 can be a microcontroller unit 111 (MCU 111), a microprocessor unit (MPU) with a memory and an IO unit, or a processor with a memory and an IO unit. In one embodiment of the present disclosure, the processor module 110 comprises a processing unit for processing data and a memory unit for storing data. The patient information can be a patient's identity (patient ID), a patient's medical history, a patient's physiological status detected by other medical/healthcare devices, etc. As the patient information is associated with the auscultation data, an auscultation file is formed by the processor module 110 and stored to the storage 170 for later use. In another embodiment of the present disclosure, the auscultation data is configured to be played by the output module 140 simultaneously during the recording of the sound from the patient's body, wherein the output module 140 comprises a speaker (not shown) for playing the auscultation data. Alternatively, the output module 140 comprises a phone jack 141 for insertion of a headset 310 with earpiece, so a medical/healthcare provider is able to listen to the sound from internal body of the patient and use the electronic stethoscope 100 to record the sound at the same time.

Continuing the discussion of the electronic stethoscope 100 in FIG. 2, the patient information is obtained by the electronic stethoscope 100 by a reader module 130, wherein the reader module 130 is a barcode reader 131. The electronic stethoscope 100 is configured to read a barcode 211 from a wristband 210 of the patient for obtaining a patient ID, and associate the patient ID with the auscultation data formed by the recorded sound from the microphone 121. As such, the patient ID and the auscultation data are stored as an auscultation file in the storage 170. Therefore, a medical/healthcare provider uses the electronic stethoscope 100 to record multiple auscultation from multiple patients and still be able to distinguish between a pluralities of auscultation file corresponding to different patients. For example, the patient ID is used as a file name for the auscultation file. Therefore, patient safety is ensured by avoiding mismatching an auscultation file of a patient to another patient's auscultation file. Although a barcode reader 131 is shown, it should be understood that a component which is capable of scanning/reading a patient information wirelessly from the patient can be used in accordance with various embodiments discussed herein. For example, the reader module 130 comprises at least one of the following: a RFID reader, a NFC reader, an Optical RFID reader, a 1D barcode reader, a 2D barcode reader, etc.

Figure 3:
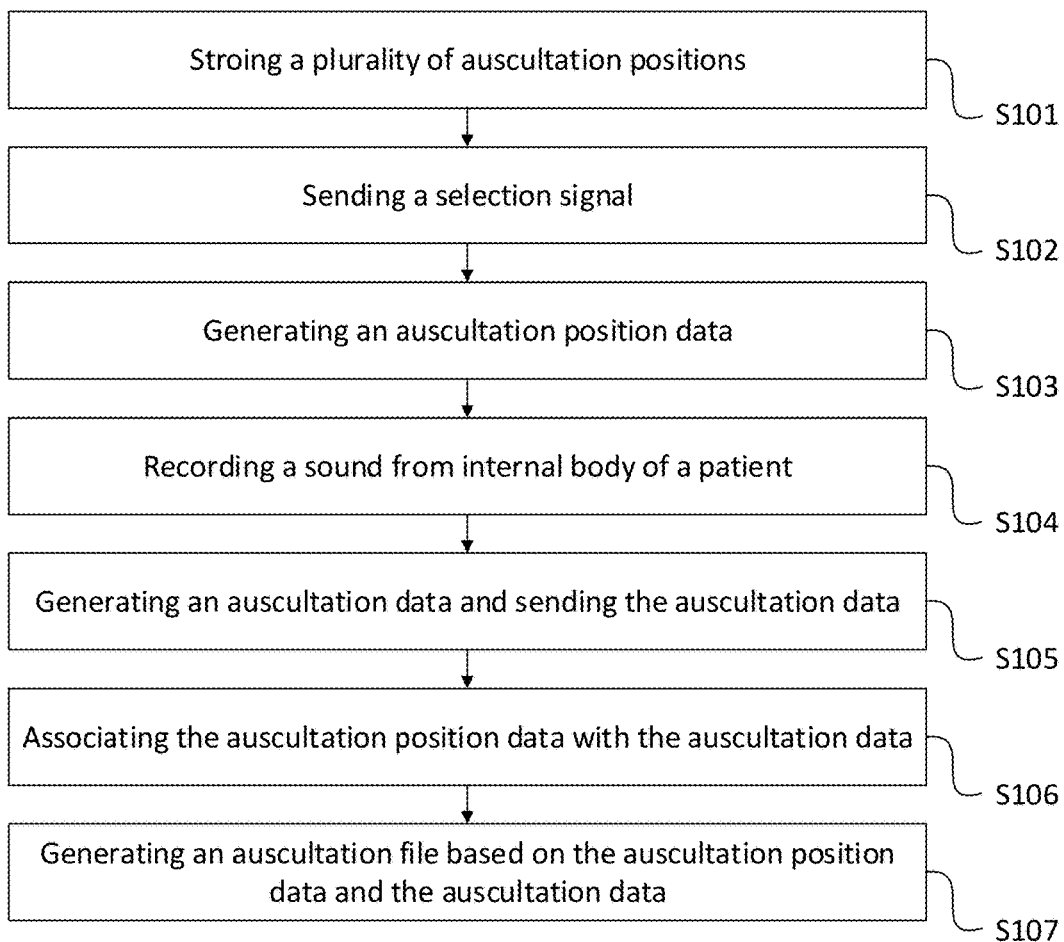
FIG. 3 is a schematic illustration of a method of obtaining an auscultation position data and an auscultation data by the electronic stethoscope according to one embodiment of the present disclosure.
Figure 4A:
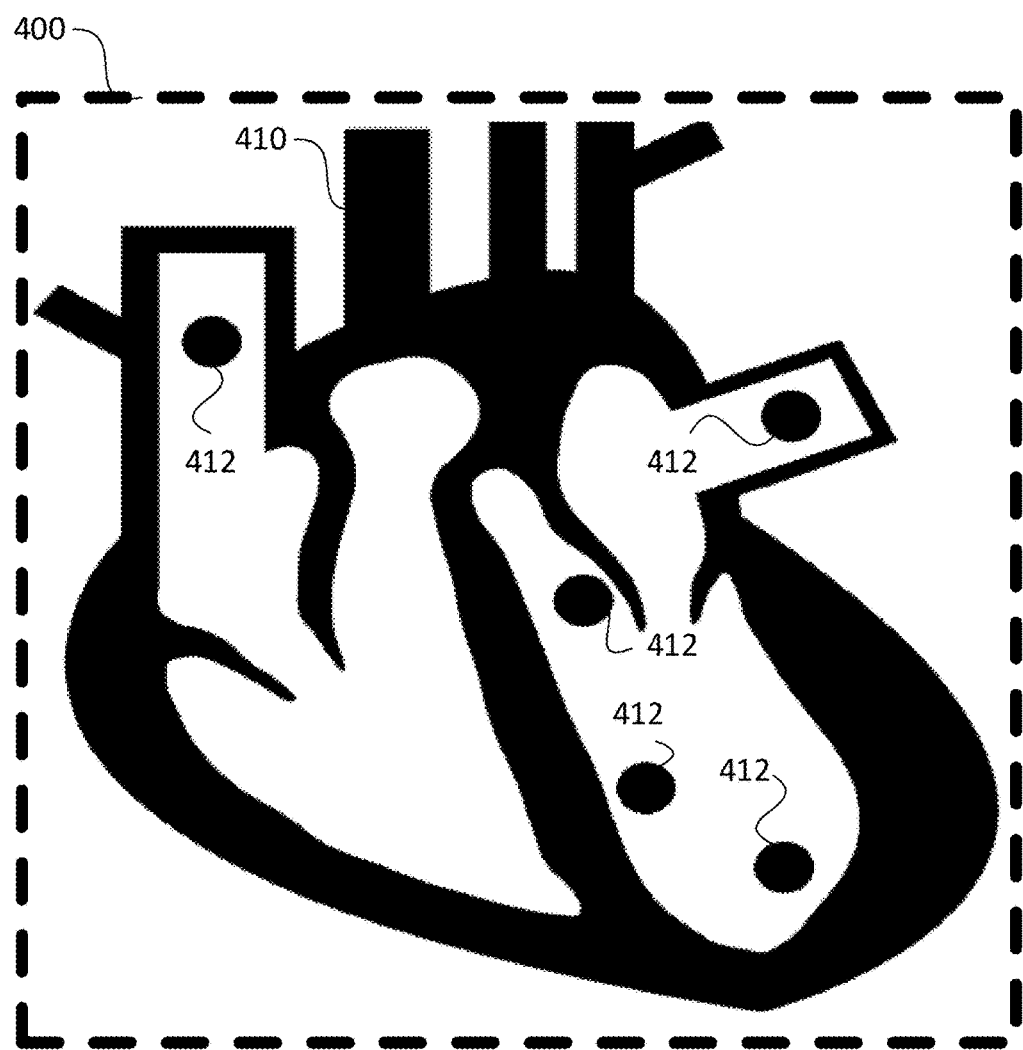
FIG. 4A-4F are a schematic illustrations of body area images with positions within the body area image corresponding to a control input interface according to one embodiment of the present disclosure.
Figure 4B:
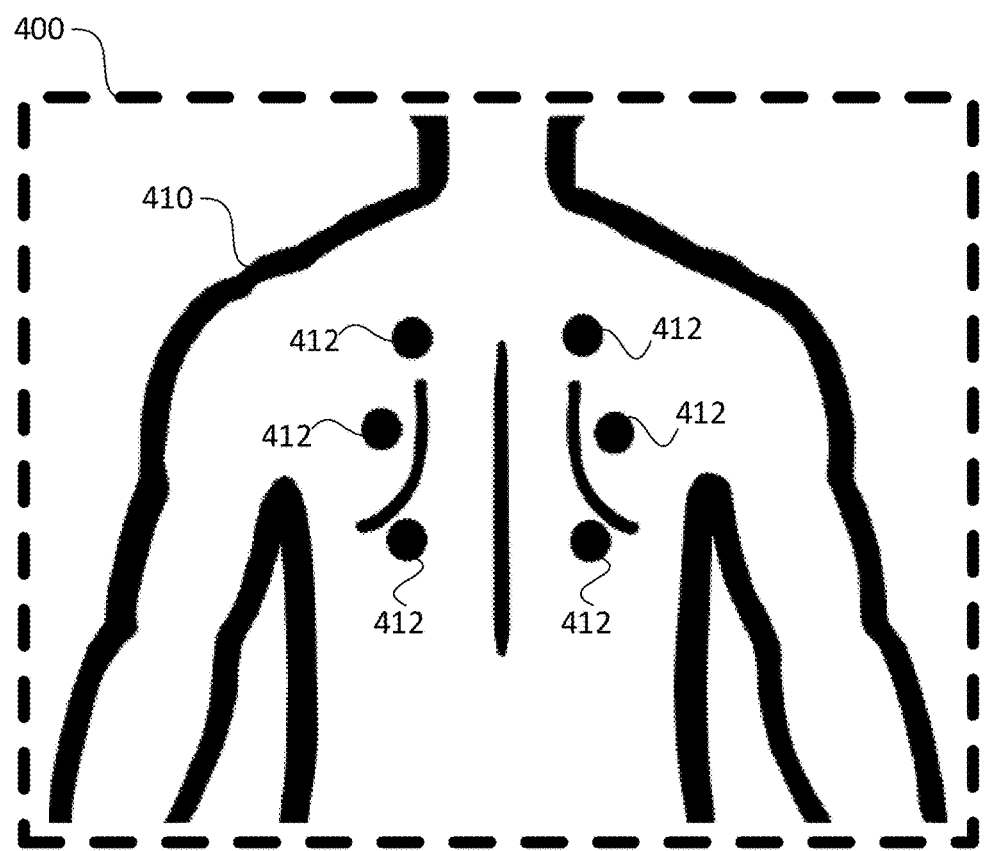
Figure 4C:
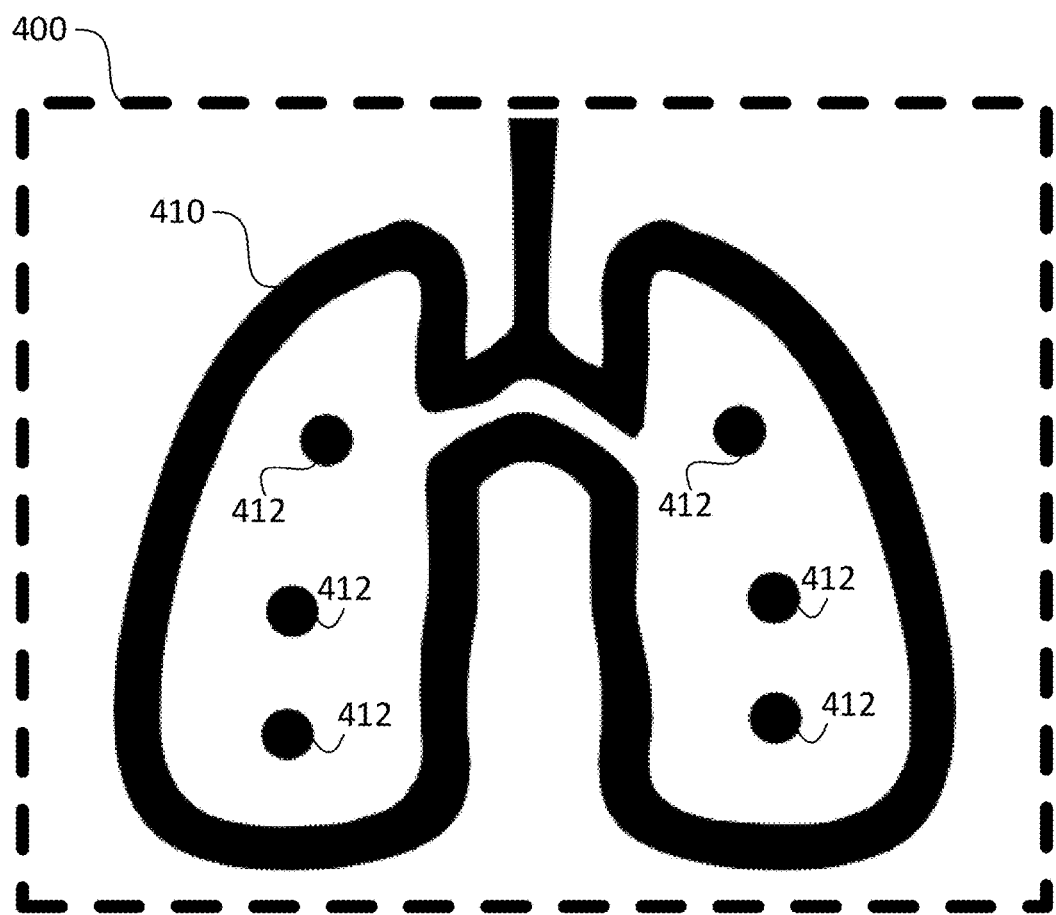
Figure 4D:
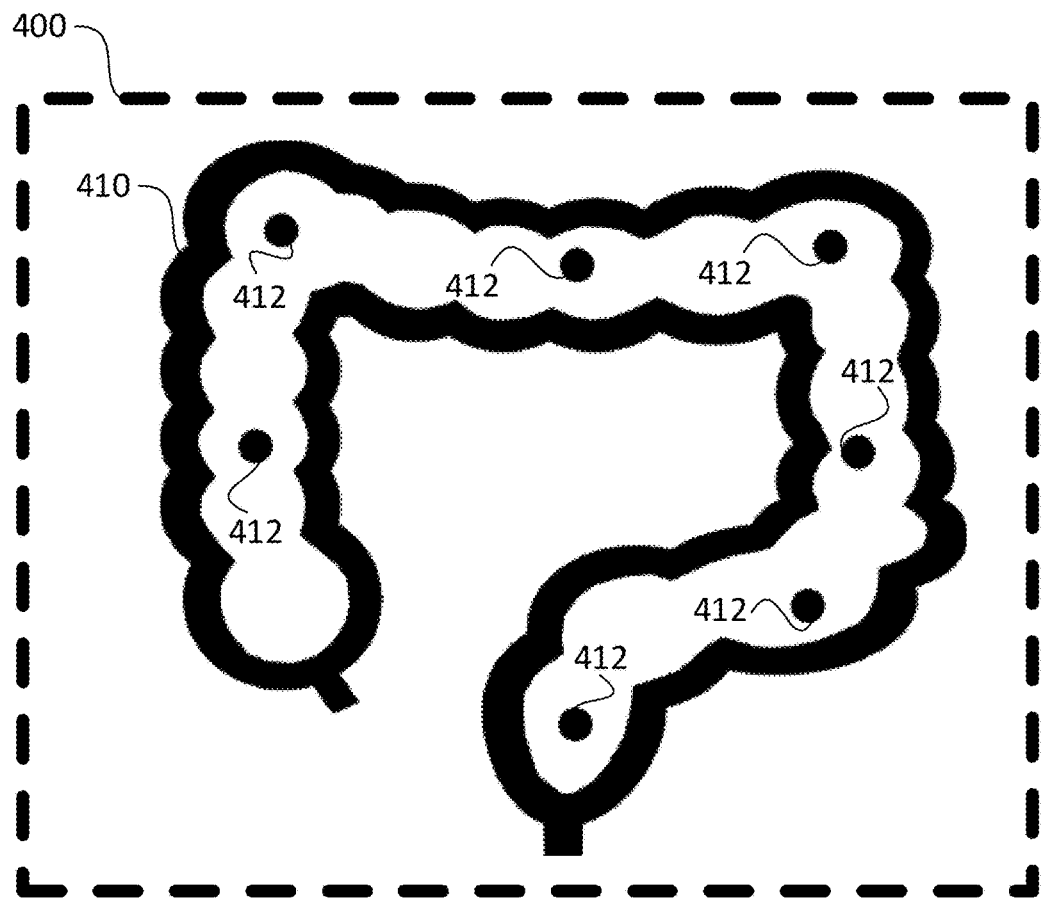
Figure 4E:
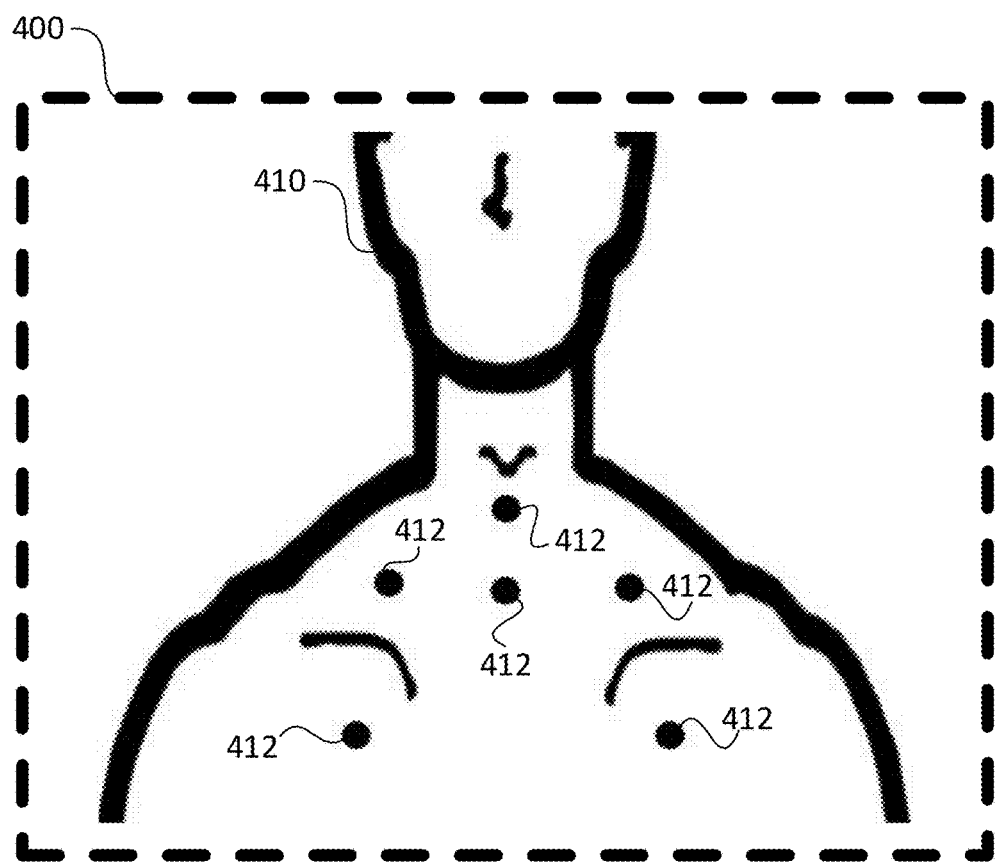
Figure 4F:
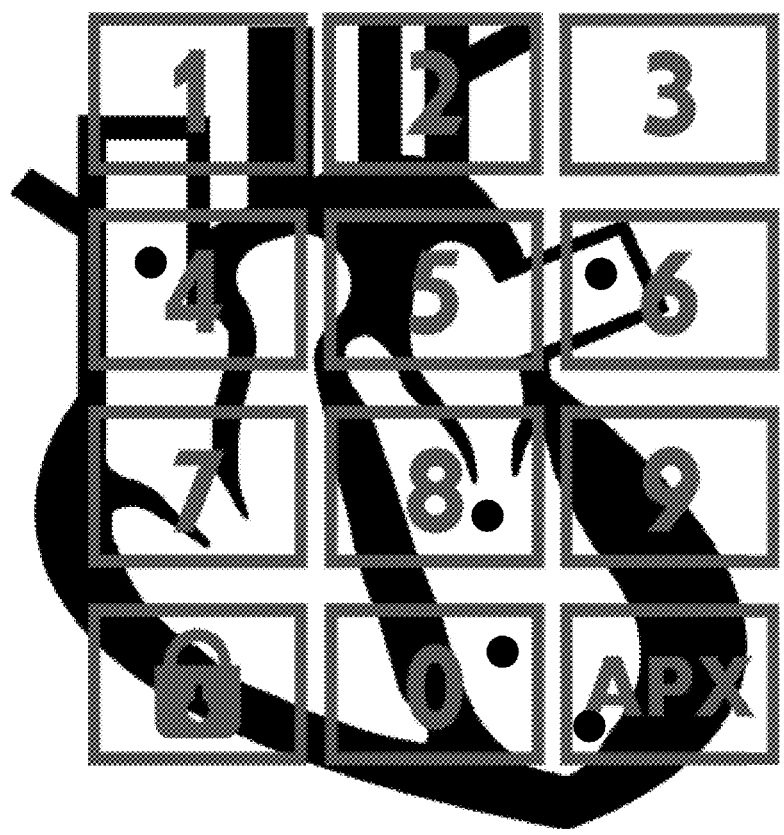

The present disclosure further provides a method to record an auscultation position 400 of a patient as shown in FIG. 3. In one embodiment of the present disclosure, in step S101, storing a plurality of auscultation positions 400 by the processor module 110. In step S102, a medical/healthcare provider selects an auscultation position 400 stored in the processor module 110 by using the control input interface 160, wherein the control input interface 160 sends a selection signal to the processor module 110. The control input interface 160 comprises various type of input component which allows the medical/healthcare provider to interact with the electronic stethoscope 100, for example a set of keypad, a touch pad, a touch panel, a rotatable input, or combinations thereof. In step S103, the processor module 110 generates an auscultation position data based on the selection signal. In step S104, the medical/healthcare provider holds the electronic stethoscope 100 against a patient's body in a position corresponding to the auscultation position 400 and record a sound from the internal body of the patient by the chestpiece 120. In step S105, the chestpiece 120 generates an auscultation data based on the sound from the internal body of the patient and sends the auscultation data to the processor module 110. In step S106, the auscultation position data is associated to the auscultation data by the processor module 110. For example, the auscultation position data is used as a file name for the auscultation file. In step S107, an auscultation file is generated by the processor module 110 based on the auscultation position data and the auscultation data. This method could be repeated multiple times for the same patient, so the medical/healthcare provider would be able to auscultate the patient at different position and record all the auscultation files without mistaking between auscultation files corresponding to different auscultation positions.

The auscultation position 400 mentioned in FIG. 3 could be further illustrated in FIG. 4A-4F according to one embodiment of the present disclosure, wherein the auscultation position 400 comprises two components, which include a body area image 410 and a position 412 within the body area image 410. As shown in FIG. 4A-4E, the body area image 410, for example, can be an image of a precordia (heart) area in FIG. 4A, a back area in FIG. 4B, a chest (lung) area in FIG. 4C, an abdomen (bowel) area in FIG. 4D, a neck area in FIG. 4E. For example in FIG. 4F, the body area image 410 of precordia area is selected, and the positions 412 within the precordia area can be selected by the corresponding control input interface 160 which is a keypad in this embodiment of the present disclosure.

In one embodiment of the present disclosure, a plurality of body area images 410 with a plurality of positions 412 within each body area image 410 is stored in the processor module 110 of the electronic stethoscope 100. The plurality of body area images 410 with a plurality of positions 412 within each body area image 410 is displayed by a display module 150. A medical/healthcare provider uses the control input interface 160 to select a body area image 410 and a position 412 within the body area image 410 among the plurality of body area images 410 with the plurality of positions 412 within each body area image 410 from the display module 150. Therefore, the control input interface 160 receives an input from the medical/healthcare provider, wherein the input is corresponding to the body area image 410 and the position 412. The control input interface 160 sends a selection signal to the processor module 110 based on the input. As such, the processor module 110 generates an auscultation position data based on the selection signal.

In another embodiment of the present disclosure, the body area image 410 and the position 412 within the body area image 410 is stored by default in the processor module 110 of the electronic stethoscope 100 and displayed by the display module 150 for selection by the medical/healthcare provider using the control input interface 160. Although the method in FIG. 3 illustrated the auscultation position 400 is selected before recording a sound from the internal body of the patient, the auscultation position 400 may also be selected after recording a sound from the internal body of the patient according to user preference of the medical/healthcare provider, as would be apparent to one of ordinary skill in the art, such as carrying out the step S101-S103 after the step S105 before the step S107.

In another embodiment of the present disclosure, the medical/healthcare provider is able to define the body area image 410 and the position 412 within the body area image 410 by importing a picture as a customized body area image 410 into the electronic stethoscope 100 via a wire transmission or wireless transmission. Once the customized body area image 410 is stored in the processor module 110, the medical/healthcare provider selects the customized body area image 410 other than body area image 410 by default. Furthermore, the electronic stethoscope 100 is configured to allow the medical/healthcare provider to designate a position on the customized body area image 410 by using the control input interface 160. For example, the wire transmission may be USB, micro USB, etc. The wireless transmission may be Bluetooth, Wi-Fi, Infrared, ZigBee, etc. Alternatively, the electronic stethoscope 100 also comprises a camera (not shown) for taking a picture of the customized body area image 410 from a patient or simple anywhere else. The camera is configured to take a picture not only as the customized body area image 410, but also as the aforementioned patient information. In the case of using a picture taken by the camera as the patient information, the picture is a portrait of the patient, wherein the portrait will be stored to the storage 170 and associated to an auscultation data to generate an auscultation file. Therefore, the medical/healthcare provider chooses the auscultation file stored in the storage 170 to play by looking at the portrait attached to the auscultation file.

Figure 5:
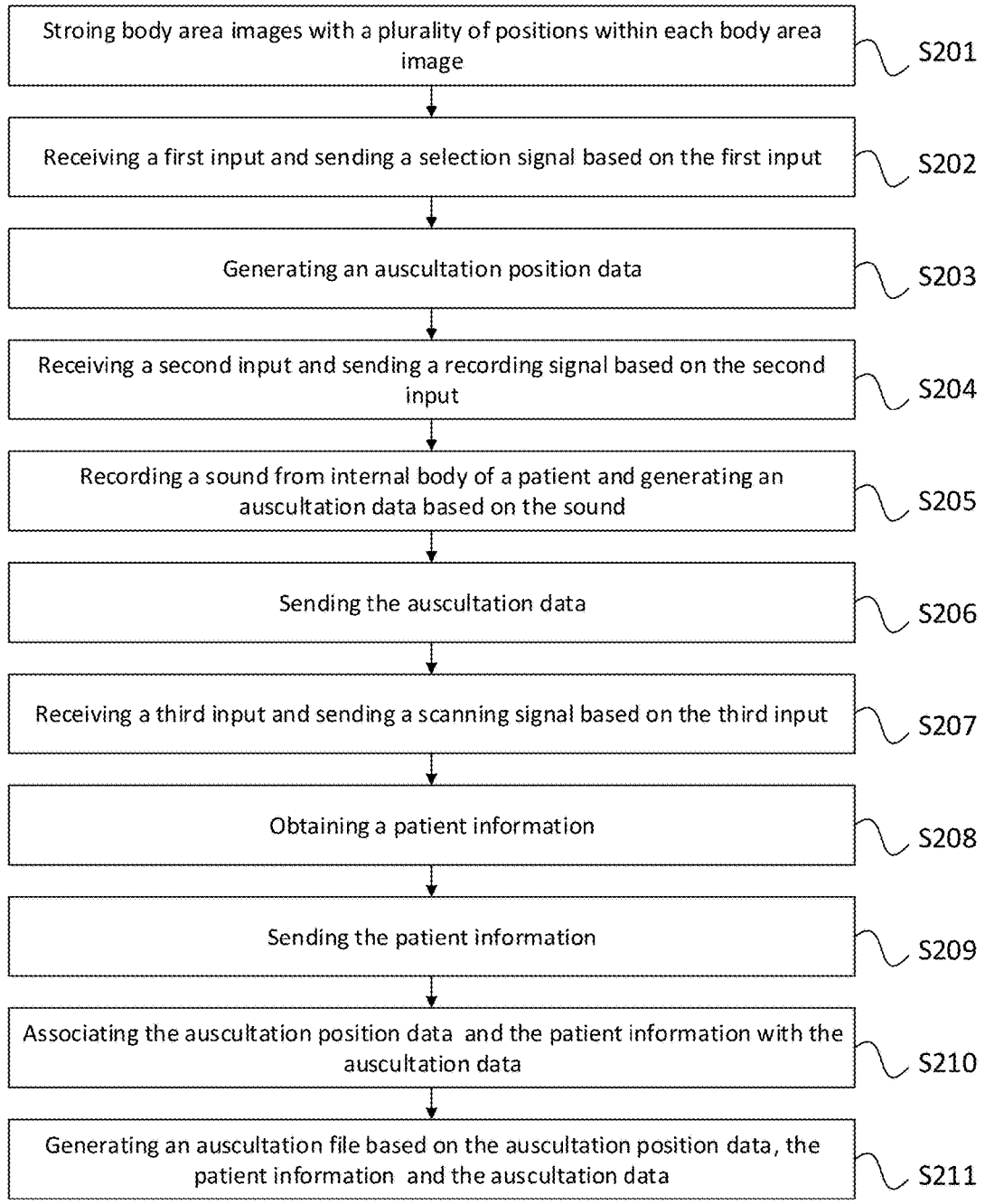
FIG. 5 is a schematic illustration of a method of obtaining a patient information, an auscultation data, and an auscultation position data by the electronic stethoscope according to one embodiment of the present disclosure.

FIG. 5 schematically illustrates a method for recording a sound, a patient information, and an auscultation position 400 by using the electronic stethoscope 100 in FIG. 2 according to one embodiment of the present disclosure. In step S201, the processor module 110 is configured to store a plurality of body area images 410 with a plurality of positions 412 within each body area image 410 by a memory unit of the processor module 110. In step S202, the control input interface 160 is configured to receive a first input from a medical/healthcare provider, wherein the first input is corresponding to a body area image 410 and a position 412 within the body area image 410 among the plurality of body area images 410 with the plurality of positions 412 within each body area image 410 in the memory unit. Then, the control input interface 160 is configured to send a selection signal to the processor module 110 based on the first input. In step S203, the processor module 110 is configured to generate an auscultation position data based on the selection signal. In step S204, the processor module 110 of the electronic stethoscope 100 is configured to receive a second input from the control input interface 160, and the processor module 110 is configured to send a recording signal to the chestpiece 120 based on the second input. In step S205, The chestpiece 120 is configured to record a sound from internal body of a patient and generate an auscultation data based on the sound in response to the recording signal. In step S206, the chestpiece 120 is configured to send the auscultation data to the processor module 110. In step S207, the processor module 110 of the electronic stethoscope 100 is configured to receive a third input from the control input interface 160, and the processor module 110 is configured to send a scanning signal to the reader module 130 based on the third input. In step 208, the reader module 130 is configured to obtain a patient information from a patient. In step S209, the reader module 130 sends the patient information to the processor module 110. In step S210, the processor module 110 is configured to associate the patient information and the auscultation position data with the auscultation data. In step S211, the processor module 110 generates an auscultation file based on the patient information, the auscultation position data, and the auscultation data. In one embodiment of the present disclosure, the processor module 110 is configured to send the auscultation file to the storage 170. The output module 140 is configured to output the sound corresponding to the auscultation data of the auscultation file.

In one embodiment of the present invention, the display module 150 is configured to display the plurality of body area images 410 with the plurality of positions 412 within each body area image 410.

In one embodiment of the present disclosure, the patient information comprises a patient ID, a personal information of the patient, etc. The personal information comprises the patient's date of birth, height, weight, blood type, gender, age, emergency contact, medical history, etc.

In one embodiment of the present disclosure, the processor module 110 of electronic stethoscope 100 is configured to receive a switch image signal from the control input interface 160 and changes a first body area image 410 to a second body area image 410 with multiple positions 412 within the second body area image 410. The processor module 110 is configured to receive a selection signal from the control input interface 160 and generate an auscultation position data by the on the second body area image 410 and a position 412 within the second body area image 410. The electronic stethoscope 100 is configured to obtain a sound from internal body of the patient using the chestpiece 120 and generates an auscultation data by the processor module 110 according to the sound. The electronic stethoscope 100 is configured to generate an auscultation file to store in the storage 170 by associating the patient information, the auscultation position data, and the auscultation data using the processor module 110.

In one embodiment of the present disclosure, the step S201-S211 could be carried out repeatedly by the medical/healthcare provider for different patients. Alternatively, the step S201-S206 could be carried out repeatedly before S207-S211 for the same patient but different auscultation positions. As such, the medical/healthcare provider is able to easily auscultate multiple patients each with different auscultation positions 400, and still be able to distinguish between multiple auscultation files. Therefore, the medical/healthcare provider is able to select a patient specific auscultation file with specific auscultation position 400 of desire for playback by using the control input interface 160.

In one embodiment of the present disclosure, the electronic stethoscope 100 is configured to display a plurality of auscultation files in a playlist by the display module 150 for the medical/healthcare provider to select for playback, wherein the display module 150 is a LCD screen, touch panel, OLED, CRT, projector, or other types of displaying components, and wherein the playlist is generated by the processor module 110 and stored in the storage 170. Once an auscultation file is selected by the medical/healthcare provider using the control input interface 160 to send a playback signal to a MCU 111, the MCU 111 sends an outputting signal to the output module 140 and obtains the auscultation file from the storage 170 based on the playback signal. Therefore, the output module 140 is configured to receive the outputting signal and the auscultation file from the MCU 111 and play the sound corresponding to the auscultation file according to the outputting signal, wherein the output module 140 can be a speaker or other audio outputting components.

In another embodiment of the present invention, the electronic stethoscope 100 is configured to store at least three playback modes in the MCU 111, for example, low frequency mode, high frequency mode, and all frequency mode. The playback modes are displayed by the display module 150 for the medical/healthcare provider to select by using the control input interface 160. As the playback mode is selected, the control input interface 160 sends a mode signal to the MCU 111, so the output module 140 is configured to play the auscultation file in a frequency range defined by the mode signal. For example, the output module 140 plays only sound below 200 Hz from the auscultation file when a low frequency mode is selected.

In one embodiment of the present disclosure, the electronic stethoscope 100 is configured to associate a time and date to an auscultation file by the processor module 110, therefore the auscultation file includes the time and date of recording. Furthermore, the auscultation file further comprises an acoustic waveform corresponding to the auscultation data which is displayed by the display module 150 during playback of the auscultation file.

Figure 6:
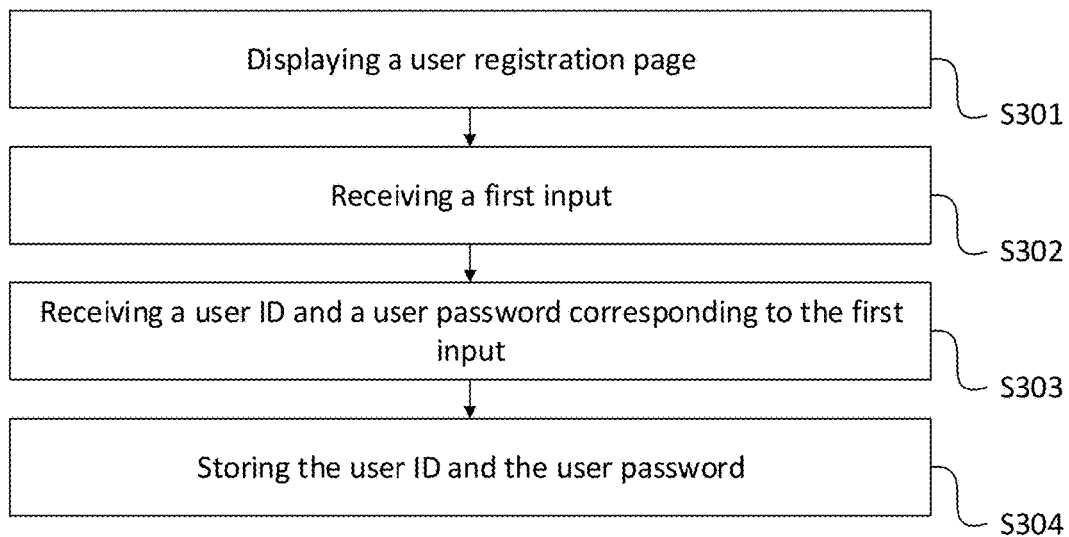
FIG. 6 is a schematic illustration of a method of registering a medical/healthcare provider to the electronic stethoscope according to one embodiment of the present disclosure.

FIG. 6 schematically illustrates a method of registering a medical/healthcare provider to the electronic stethoscope 100 according to one embodiment of the present disclosure. Under medical/healthcare environment, not only keeping a full record of a patient but also restricting access to the record of the patient is important. The electronic stethoscope 100 is configured to be personalized to a medical/healthcare provider for keeping the patient related information secured. This could be achieved by apply the method in FIG. 6. In step S301, the electronic stethoscope 100 is configured to display a user registration page by the display module 150, wherein the user registration page comprises a user ID field and a user password field. In step S302, the control input interface 160 is configured to receive a first input from the medical/healthcare provider. In step S303, the processor module 110 is configured to receive a user ID and a user password corresponding to the first input from the control input interface 160. In step S304, the electronic stethoscope 100 is configured to store the user ID and the user password from the control input interface 160 into the processor module 110 for later use, such as user verification. The user ID may be the medical/healthcare provider's employee number, name, or other customized user ID comprising numbers and/or characters. The user password may be a numbers and/or characters, a drawing pattern, a facial image, a fingerprint or combinations thereof. It should be apparent to anyone having ordinary skill in the art that similar process may be carried out repeatedly for registering multiple medical/healthcare providers to the same electronic stethoscope 100.

In one embodiment of the present disclosure, the user ID and the user password is used for user verification under various situations such as turning on the power of the electronic stethoscope 100, waking up the electronic stethoscope 100 from sleep mode, recording a sound from internal body of a patient, playing an auscultation file. For example, in the case of turning on the power of a locked electronic stethoscope 100. The electronic stethoscope 100 is configured to receive a power on signal from the control input interface 160, and display a user verification page by the display module 150, wherein the user verification page comprises a user ID field and a user password field. As a registered medical/healthcare provider entering a user ID and user password by the control input interface 160, the MCU 111 is configured to compare the user ID and user password to all registered user ID and password stored in the MCU 111. Once the comparison result is a match, the MCU 111 is configured to unlock the electronic stethoscope 100. It should be apparent to anyone having ordinary skill in the art that similar process may be carried out for all the other situations where user verification is needed.

In another embodiment of the present disclosure, a user ID is associated to all auscultation file that is generated after a medical/healthcare provider corresponding to the user ID recording a sound from internal body of a patient. In this case, restriction of playing an auscultation file is applied that the medical/healthcare provider is only able to play the auscultation file that is associated with the medical/healthcare provider's user ID. This restriction is especially useful under certain circumference such as multiple medical/healthcare providers are registered to the same electronic stethoscope 100. It should be apparent to anyone having ordinary skill in the art that similar restriction may be carried out for recording a sound from internal body of a patient when the patient information is associated with the user ID such that only the medical/healthcare provider with the user ID could be able to start recording.

Figure 7:
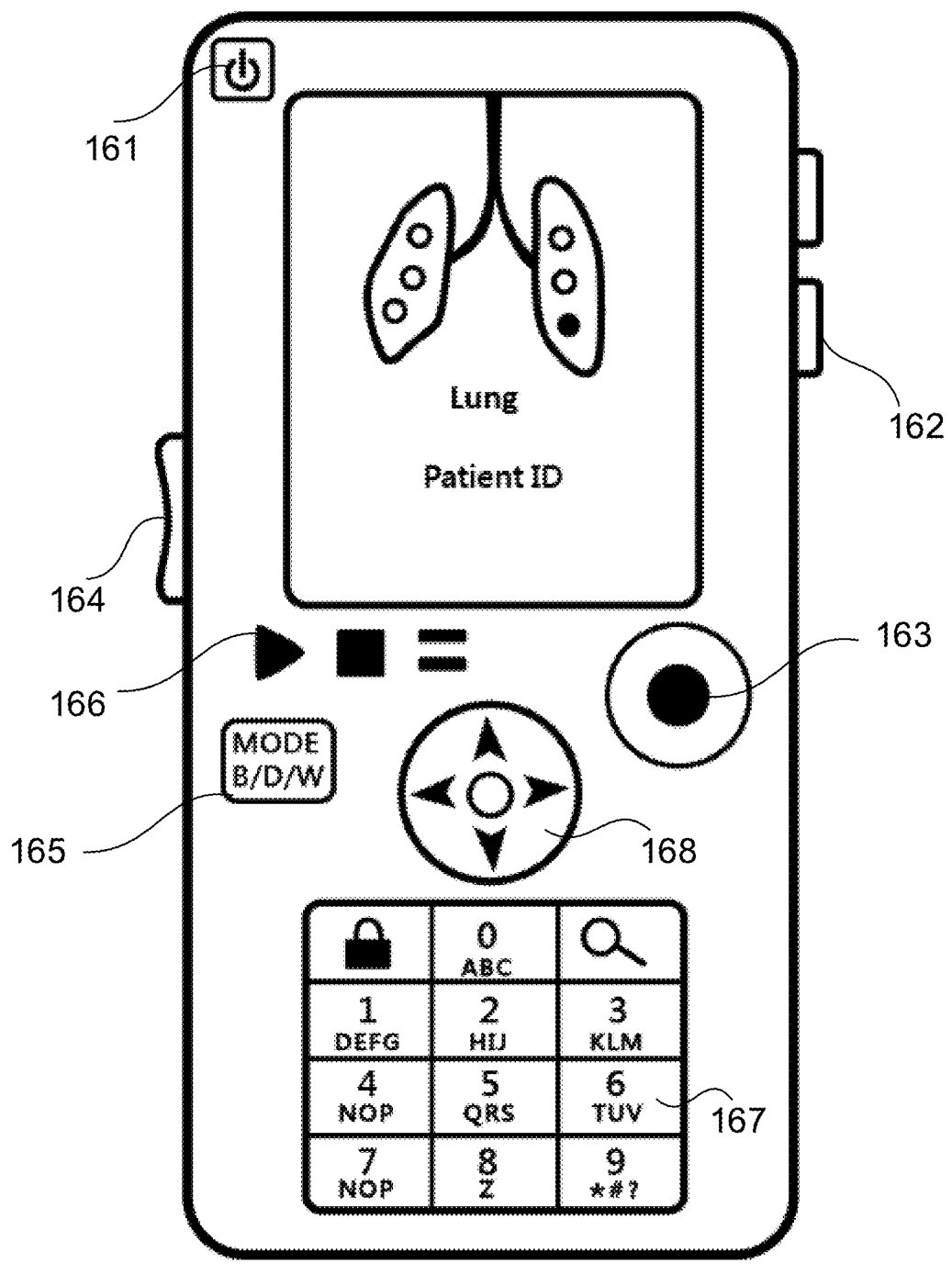
FIG. 7 is a schematic illustration of a control input interface of the electronic stethoscope according to one embodiment of the present disclosure.

FIG. 7 schematically illustrates a control input interface 160 of the electronic stethoscope 100 according to one embodiment of the present disclosure. The control input interface 160 is configured to comprise various different controls that allow a medical/healthcare provider to actuate the various different controls to realize various different functionalities of the electronic stethoscope 100. For example, a power control 161 for sending a power on signal to turn on the electronic stethoscope 100, a volume control 162 for controlling the volume of electronic stethoscope 100 when playing an auscultation file, recording control 163 for sending a recording signal to start recording a sound from internal body of a patient, scanning control 164 for actuating the reader module 130 to obtain a patient information from the patient, playback mode control 165 for switching between different playback modes, playback control 166 for sending a playback signal to control the playback of an auscultation file, selection control 167 for sending selection signal to select auscultations files and/or body area images 410 and/or position 412 within the body area images 410, switch image control 168 for sending switch image signal to switch between different body area images 410. The playback control 166 not only allows the medical/healthcare provider to play an auscultation file, but also performs other functions such as, stop, rewind, repeat all, A-B repeat, repeat once, etc. In another case, the control input interface 160 further comprises a delete control (not shown) for deleting at least one auscultation file or patient information. It should be noted that the above example is not to limit the present disclosure, so controls that are not mentioned may also be applied in the electronic stethoscope 100 to allow other functionalities.

In one embodiment of the present disclosure, the above control input interface 160 may be a plurality of buttons, a touch panel with a plurality of functionality icons, a touch pad, a rotatable input, a voice control module, optical sensor, or combinations thereof, wherein the optical sensor may be a camera which provides image recognition such as gesture recognition. When it comes to voice control, the electronic stethoscope 100 further comprises a voice control module (not shown), wherein the various functionalities of controls mentioned is activated by a plurality of voice commands. For example, a voice command as "Recording" activates the function of the recording control 163.

In one embodiment of the present disclosure, the electronic stethoscope 100 further comprises a wireless module (not shown) to enable wireless communication. The wireless module may be a Bluetooth module, Wi-Fi module, Infrared module, ZigBee module, WiMAX module, 3G module, 4G module, etc. For example, the electronic stethoscope 100 comprises a Bluetooth wireless module for establishing a communication with a Bluetooth headset, wherein the Bluetooth headset is used to play an auscultation file wirelessly. It should be noted that, a wireless speaker may be used as well. Alternatively, the Bluetooth headset is configured to allow the electronic stethoscope 100 to record a patient information, such as voice diagnosis and/or description, by the medical/healthcare provider. It should be apparent to anyone having ordinary skill in the art that an ordinary headset with microphone 121 or other similar components that may be used instead of the Bluetooth headset.

Figure 8:
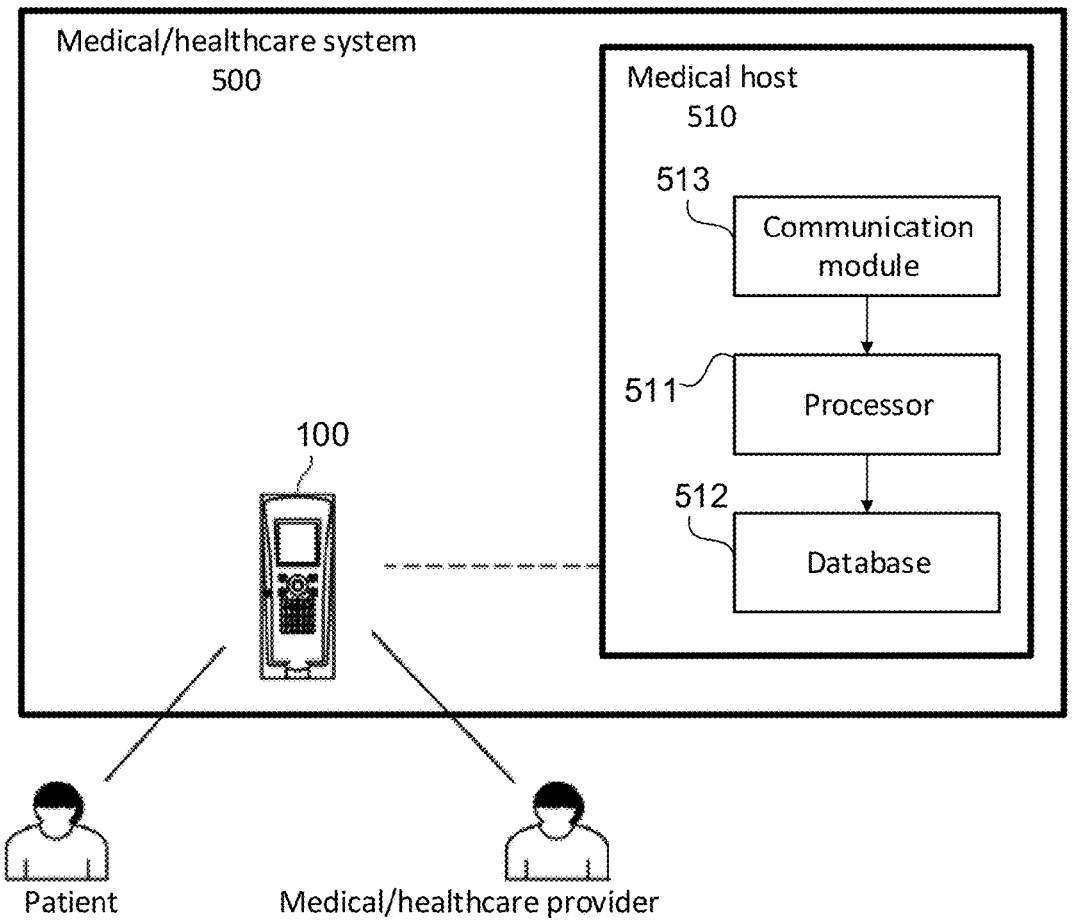
FIG. 8 is a schematic illustration of a medical/healthcare system comprising the electronic stethoscope according to one embodiment of the present disclosure.

FIG. 8 schematically illustrates a medical/healthcare system in one embodiment of the present disclosure, a medical/healthcare system 500 is disclosed therein. The medical/healthcare system 500 comprises the electronic stethoscope 100, and a medical host 510, wherein the electronic stethoscope 100 is connected to the medical host by wired and/or wirelessly to enable data transmission in between. For example, the aforementioned auscultation data, patient information, auscultation position data, and auscultation file are sent to the medical host via a Wi-Fi module (not shown) of the electronic stethoscope 100. The medical host 510 comprises a processor 511, a database 512, and a communication module 513, wherein the communication module 513 is configured to enable wire and/or wireless data transmission. Therefore, the medical host 510 is configured to receive and store the auscultation data, patient information, auscultation position data, and auscultation file from the electronic stethoscope 100 into the database 512 via the communication module 513. By doing so, all the data contained by the electronic stethoscope 100 is stored within the medical host 510, so the electronic stethoscope 100 is configured to access to the database 512 of the medical host 510 to download at least one aforementioned auscultation data, patient information, auscultation position data, and auscultation file uploaded by another electronic stethoscope 100.

In one embodiment of the present disclosure, the power module is a rechargeable or non-rechargeable battery. In the case of rechargeable battery, the electronic stethoscope 100 comprises a charging port (not shown) for charging the rechargeable battery. Alternatively, the electronic stethoscope 100 further comprises a wireless charging dock station for charging the electronic stethoscope 100 wirelessly for convenience to the medical/healthcare provider.

In one embodiment of the present disclosure, the aforementioned storage 170 may be various types of memory technology, such as RAM, ROM, EEPROM, flash memory, optical storage, magnetic disk storage or other magnetic storage devices, or other medium which is configured to store the desired information and be accessed by the electronic stethoscope 100.

Previous descriptions are only embodiments of the present disclosure and are not intended to limit the scope of the present disclosure. Many variations and modifications according to the claims and specification of the disclosure are still within the scope of the claimed disclosure. In addition, each of the embodiments and claims does not have to achieve all the advantages or characteristics disclosed. Moreover, the abstract and the title only serve to facilitate searching patent documents and are not intended in any way to limit the scope of the claimed disclosure.

What is claimed is:
1. An electronic stethoscope, comprising:
a reader module for obtaining a patient information from a patient;
as chestpiece for obtaining sounds from the patient;
a control input interface for receiving a user identification (ID) and a user password;
a processor module electrically connected to the reader module, the chestpiece, and the control input interface for receiving and storing the patient information, the user ID and the user password, forming an auscultation data according to the sounds, associating the patient information to an auscultation data to form an auscul- tation file and performing user verification according to the user ID and the user password; and an output module electrically connected to the processor module for outputting the sounds according to the auscultation file, wherein the control input interface is further configured for sending a playback signal to the processor module, the processor module is further configured for sending an outputting signal to the output module based on the playback signal, the output module is further configured for playing the auscultation file when receiving the outputting signal, the control input interface is further configured for receiving an input corresponding to a body area image of the patient and a plurality of positions within the body area image, and sending a selection signal to the processor module based on the input the processor module is further configured for generating an auscultation position data based on the selection signal, the auscultation file comprises the auscultation position data, the processor module is further configured for storing a plurality of playback modes, the output module is further configured for outputting the sounds under one of the playback modes, and the playback modes have different sound frequency ranges, and the playback signal is associated with the user ID and the user password, the body area image of the patient, the plurality of positions within the body area image, the selection signal, the auscultation position data and the playback modes.

2. The electronic stethoscope according to claim 1, further comprising a display module configured for displaying a playlist containing the auscultation file.

3. The electronic stethoscope according to claim 1, wherein the chestpiece comprises a microphone and a diaphragm.

4. The electronic stethoscope according to claim 1, herein the patient information comprises a patient ID, a medical history, a date of birth, a height, a weight, a blood type, a gender, an age, an emergency contact, or any combination thereof.

5. The electronic stethoscope according to claim 1, wherein the reader module is a barcode reader configured for reading at least one of an one-dimensional (1D) barcode and a two-dimensional (2D) barcode.

6. The electronic stethoscope according to claim 1, wherein the output module is a phone jack.

7. The electronic stethoscope according to claim 1, wherein the output module is further configured for outputting the sounds of the auscultation data corresponding to the auscultation file during the obtaining the sounds of the patient by the chestpiece.

8. The electronic stethoscope according to claim 4, wherein the patient ID comprises a file name of the auscultation file.

9. The electronic stethoscope according to claim 1, wherein the positions corresponds to where the sounds are obtained.

10. The electronic stethoscope according to claim 1, further comprising a camera for taking a portrait of the patient, wherein the portrait is associated to the auscultation data.

11. The electronic stethoscope according to claim 1, further comprising a display module for displaying the body area image and the positions within the body area image, wherein the body area image and the positions are stored in the processor module.

12. The electronic stethoscope according to claim 1, wherein the auscultation file comprises a time and a date of obtaining the sounds in the auscultation data.

13. The electronic stethoscope according to claim 1, wherein the user ID is associated to the auscultation data.

14. The electronic stethoscope according to claim 1, further comprising a Bluetooth module for playing the auscultation file wirelessly.

15. The electronic stethoscope according to claim 1, further comprising a wireless module for sending the auscultation file to a medical host wirelessly.

16. An electronic stethoscope, comprising:
a chestpiece for obtaining sounds from a patient;
a control input interface for receiving an input corresponding to a body area image and a plurality of positions within the body area image, sending a selection signal according to the input, and receiving a user identification (ID) and a user password;
a processor module electrically connected to the chestpiece and the control input interface for storing the user ID and the user password, the body area image and the positions within the body area image, generating an auscultation position data based on the selection signal, associating the auscultation position data to the auscultation data to form an auscultation file, and performing user verification according to the user ID and the user password; and
an output module electrically connected to the processor module for outputting the sounds according to the auscultation file,
wherein the control input interface is further configured for sending a playback signal to the processor module, the processor module is further configured for sending an outputting signal to the output module based on the playback signal, the output module is further configured for playing the auscultation file when receiving the outputting signal,
the processor module is further configured for storing a plurality of playback modes, the output module is configured for outputting the sounds under one of the playback modes, the playback modes have different sound frequency ranges, and
the playback signal is associated with the user IL) and user password the body area image, the plurality of positions within the body area image, the selection signal, the auscultation position data, and the playback modes.

17. The electronic stethoscope according to claim 16, further comprising a display module configured for displaying a play list containing the auscultation file.

18. The electronic stethoscope according to claim 16, wherein the chestpiece comprises a microphone and a diaphragm.

19. The electronic stethoscope according to claim 16, wherein the patient information comprises a patient ID, a medical history, a date of birth, a height, a weight, a blood type, a gender, an age, an emergency contact, or any combination thereof.

20. The electronic stethoscope according to claim 16, further comprising a reader module configured for obtaining a patient information from the patient, wherein the patient information is associated to the auscultation data by the processor module.

21. The electronic stethoscope according to claim 20, wherein the reader module is a barcode reader configured for reading at least one of a ID barcode and a 2D barcode.

22. The electronic stethoscope according to claim 20, wherein the patient information comprises a patient ID, and the patient ID comprises a file name of the auscultation file.

23. The electronic stethoscope according to claim 16, wherein the output module is a phone jack.

24. The electronic stethoscope according to claim 16, wherein the output module is further configured for outputting the sounds of the auscultation data corresponding to the auscultation file during the obtaining the sounds the patient by the chestpiece.

25. The electronic stethoscope according to claim 20, wherein the patient information further comprises the body area image and the positions within the body area image, and the positions correspond to where the sounds are obtained.

26. The electronic stethoscope according to claim 16, further comprising a camera for taking a portrait of the patient, wherein the portrait is associated to the auscultation data.

27. The electronic, stethoscope according to claim 16, further comprising a display module for displaying the body area image and the positions within the body area image.

28. The electronic stethoscope according to claim 16, wherein the auscultation file comprises a time and a date of Obtaining the sounds in the auscultation data.

29. The electronic stethoscope according to claim 16, wherein the user ID is associated to the auscultation data.

30. The electronic stethoscope according to claim 16, further comprising a Bluetooth module for playing the auscultation file wirelessly.

31. The electronic stethoscope according to claim 16, further comprising a wireless module for sending the auscultation file to a medical host wirelessly.

32. A method of auscultation implemented by an electronic stethoscope, comprising:
  receiving a user ID and a user password by a control input interface of the electronic stethoscope;
  performing user verification according to the user ID and the user password by a processor module of the electronic stethoscope;
  storing a plurality of body area images and a plurality of positions within each of the body area images by the processor module;
  receiving a first input by the control input interface, wherein the first input corresponds to one of the body area images and a plurality of positions within the body area image;
  sending a selection signal to the processor module by the control input interface based on the first input;
  generating an auscultation position data by the processor module based on the selection signal;
  receiving a second input by the processor module from the control input interface;
  sending an obtaining signal by the processor module to a chestpiece based on the second input;
  obtaining sounds from a patient by the chestpiece in response to the obtaining signal;
  generating an auscultation data corresponding to the sounds by the chestpiece;
  sending the auscultation data by the chestpiece to the processor module;
  associating the auscultation position data to the auscultation data and forming an auscultation file based on the auscultation position data and the auscultation data by the processor module;
  receiving a mode signal from the control input interface by the processor module; and
  outputting sounds corresponding to the auscultation data in the auscultation file by an output module in a frequency range defined by the mode signal,
  wherein the mode signal is associated with user ID and user password, the plurality of body area images, the plurality of positions within the body area image, the selection signal, the auscultation position data.

33. The method of auscultation according to claim 32, further comprising:
  sending the auscultation file to a storage of the electronic stethoscope by the processor module; and
  outputting the sounds corresponding to the auscultation data in the auscultation file by an output module of the electronic stethoscope.

34. The method of auscultation according to claim 33, wherein the outputting module is a phone jack.

35. The method of auscultation according to claim 32, further comprising: displaying the body area images and the positions within each of the body area image by a display module.

36. The method of auscultation according to claim 32, further comprising:
  receiving a third input from the control input interface by the processor module;
  sending a scanning signal to a reader module based on the third input by the processor module;
  obtaining a patient information of the patient by the reader module based on the scanning signal; and
  sending the patient information to the processor module by the reader module;
  associating the patient information to the auscultation data by the processor module.

37. The method of auscultation according to claim 36, wherein the patient information comprises a patient ID, a medical history, a date of birth, a height, a weight, a blood type, a gender, an age, an emergency contact, or any combination thereof.

38. The method of auscultation according to claim 36, wherein the reader module is configured for reading at least one of a ID barcode and a 2D barcode.

39. The method of auscultation according to claim 32, further comprising: receiving the auscultation file in the storage by, a communication module of a medical host.

40. The method of auscultation according to claim 32, wherein the auscultation comprises a date and a time of obtaining the sounds in the auscultation data.

41. The method of auscultation according to claim 32, further comprising: storing the user ID and the user password and associating the user ID and the user password to the auscultation data by the processor module.

42. The method of auscultation according to claim 32, further comprising: outputting the sounds by an output module during obtaining the sounds the patient by the chestpiece.

* * * * *